US012576248B2

(12) United States Patent
Ida et al.

(10) Patent No.: US 12,576,248 B2
(45) Date of Patent: Mar. 17, 2026

(54) GUIDE WIRE

(71) Applicant: Asahi Intecc Co., Ltd., Seto (JP)

(72) Inventors: Kousuke Ida, Seto (JP); Kanako Nishio, Seto (JP); Masaaki Shigematsu, Seto (JP)

(73) Assignee: ASAHI INTECC CO. , LTD., Seto (JP)

( * ) Notice: Subject to any disclaimer, the term of this patent is extended or adjusted under 35 U.S.C. 154(b) by 597 days.

(21) Appl. No.: 18/110,380

(22) Filed: Feb. 16, 2023

(65) Prior Publication Data

US 2023/0191087 A1 Jun. 22, 2023

Related U.S. Application Data

(63) Continuation of application No. PCT/JP2021/017634, filed on May 10, 2021.

(30) Foreign Application Priority Data

Aug. 25, 2020 (JP) ................................. 2020-141387

(51) Int. Cl.
*A61M 25/09* (2006.01)

(52) U.S. Cl.
CPC .................................... *A61M 25/09* (2013.01)

(58) Field of Classification Search
CPC ........ A61M 25/09; A61M 2025/09083; A61M 2025/09175
See application file for complete search history.

(56) References Cited

U.S. PATENT DOCUMENTS

| 5,885,227 | A | 3/1999 | Finlayson |
| 6,669,652 | B2 | 12/2003 | Anderson et al. |
| 2012/0310217 | A1 | 12/2012 | Maki |
| 2012/0323145 | A1 | 12/2012 | Nagano et al. |

FOREIGN PATENT DOCUMENTS

| JP | 2013-268 | A | 1/2013 |
| JP | 2013-111320 | | 6/2013 |
| JP | 2013-176488 | A | 9/2013 |
| JP | 5392792 | B2 | 1/2014 |

OTHER PUBLICATIONS

International Search Report and Written Opinion mailed on Jun. 8, 2021, received for PCT Application PCT/JP2021/017634, filed on May 10, 2021, 9 pages including English Translation.

*Primary Examiner* — Justin Xu
(74) *Attorney, Agent, or Firm* — XSENSUS LLP

(57) ABSTRACT

A guide wire includes a core shaft, a coil body that covers the core shaft, and a distal end side joint part that joins the distal end of the coil body and the distal end of the core shaft. The distal end side joint part has a substantially truncated cone-shaped outer diameter decreasing portion whose outer diameter decreases toward the distal end direction, and a substantially spherical segment-shaped most distal end portion at the distal end of the outer diameter decreasing portion and whose outer diameter decreases towards the distal end direction. Height $r1$ of the most distal end portion, outer diameter $r2$ of the bottom surface of the most distal end portion, and height $r3$ of the outer diameter decreasing portion satisfy the following equations (1) and (2).

$$0.33 < r1/r2 < 0.63 \tag{1}$$

$$2.5 < r3/r2 < 3.8 \tag{2}$$

10 Claims, 8 Drawing Sheets

FIG.6

GUIDE WIRE

CROSS-REFERENCE TO RELATED APPLICATIONS

This application is a continuation application of International Application No. PCT/JP2021/017634, filed May 10, 2021, which claims priority to Japanese Application No. 2020-141387, filed in the Japanese Patent Office on Aug. 25, 2020, the entire contents of both of which being incorporated herein by reference.

TECHNICAL FIELD

The technology disclosed herein relates to a guide wire for guiding a medical device to a target position in a body cavity.

BACKGROUND

Methods using catheters are widespread as methods for treating or testing constricted parts or occluded parts (hereinafter referred to as "lesion(s)") of blood vessels. A guide wire is generally used for guiding a catheter to an intravascular lesion. The guide wire includes a core shaft, a coil body that covers the core shaft, and a distal end side joint part that joins the distal end of the coil body and the distal end of the core shaft.

Some guide wires are intended to penetrate a relatively hard lesion such as Chronic Total Occlusion (also abbreviated as "CTO".), for example. Such guide wires are required to have high penetration performance in order to ensure it to penetrate such a lesion. In order for a guide wire to have high penetration performance, a guide wire including the distal end portion of a coil body in a tapered shape and the distal end joint part in a tapered shape is known (see, for example, Patent Literature 1).

CITATION LIST

Patent Literature

Patent Literature 1: U.S. Pat. No. 6,669,652

SUMMARY

Technical Problems

As described above, a guide wire intended to penetrate a hard lesion is required to have high penetration performance. On the other hand, a guide wire having an excessively high penetration performance increases a risk of accidentally damaging blood vessels. Therefore, a guide wire is required to have an appropriate range of penetration performance, so that it can reliably penetrate even a relatively hard lesion while avoiding damaging blood vessels. Conventionally, no configuration has been proposed for a guide wire to have such an appropriate range of penetration performance.

Technology capable of solving the above problems is disclosed herein.

Solutions to Problems

The technology disclosed herein can be implemented as the following aspects, for example.

The guide wire disclosed herein includes a core shaft, a coil body that covers the core shaft, and a distal end side joint part that joins the distal end of the coil body and the distal end of the core shaft. The distal end side joint part has a substantially truncated cone-shaped outer diameter decreasing portion whose outer diameter decreases toward the distal end direction, and a substantially spherical segment-shaped most distal end portion which is provided at the distal end of the outer diameter decreasing portion and whose outer diameter decreases toward the distal end direction. Height r1 of the most distal end portion, outer diameter r2 of the bottom surface of the most distal end portion, and height r3 of the outer diameter decreasing portion satisfy the following equations (1) and (2).

$$0.33 < r1/r2 < 0.63 \tag{1}$$

$$2.5 < r3/r2 < 3.8 \tag{2}$$

The guide wire can realize an appropriate range of penetration performance such that it can reliably penetrate even a relatively hard lesion while avoiding damaging body cavities.

Note that the technology disclosed herein can be achieved in various forms, such as guide wires and methods for producing the same.

BRIEF DESCRIPTION OF DRAWINGS

FIG. 6 is a graph showing the measurement results obtained under conditions same as those under which the results in FIG. 4 were obtained.

DESCRIPTION OF EMBODIMENTS

A. Embodiment

Figure 1:
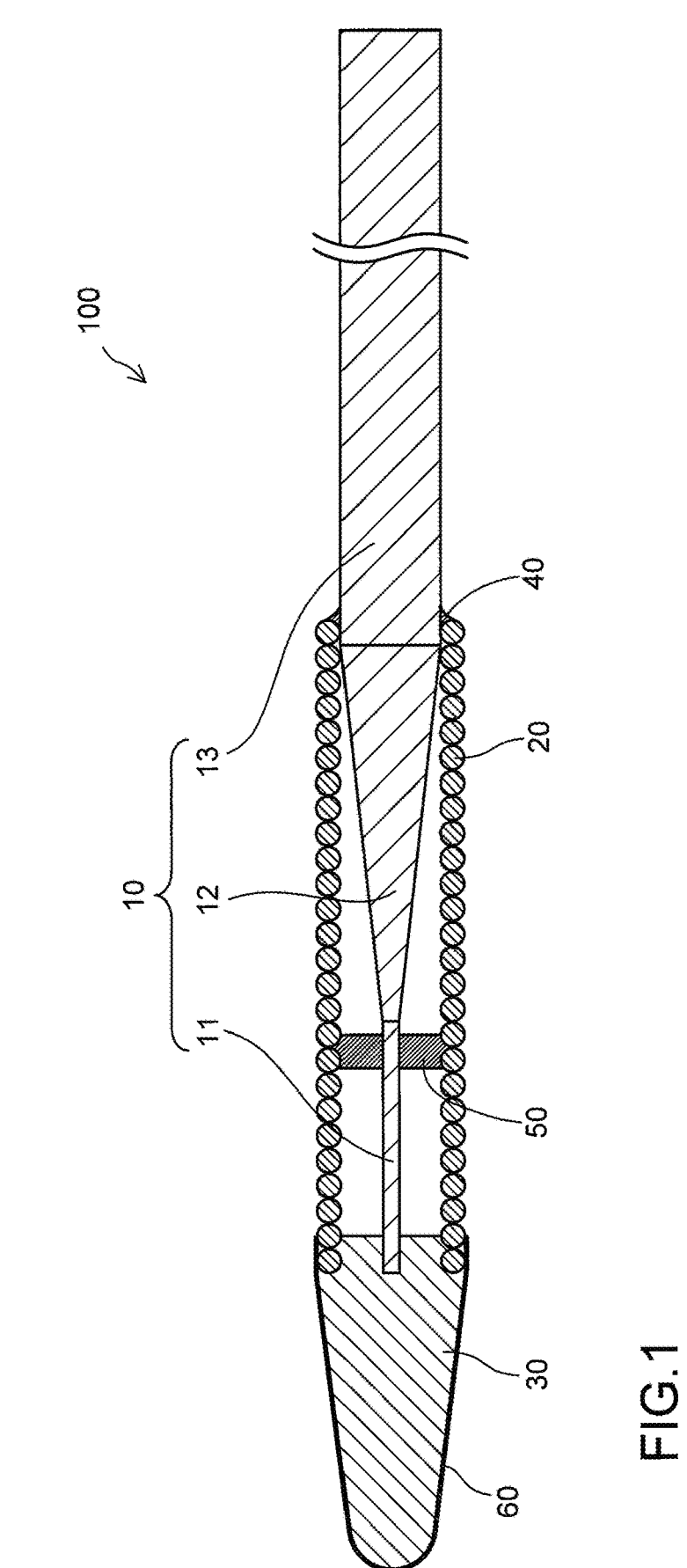
FIG. 1 is a diagram that schematically shows the configuration of a guide wire in the embodiment.

A-1. Configuration of Guide Wire:

FIG. 1 is a diagram that schematically shows the configuration of the guide wire in the embodiment. FIG. 1 shows a longitudinal cross section (YZ cross section) of a guide wire 100. Z axis positive direction side is the distal end side (distal side) to be inserted to a body, and Z axis negative direction side is the proximal end side (proximal side, near side) to be manipulated by a professional such as a doctor. In FIG. 1, a portion of the guide wire 100 is omitted. The same applies to the following figures. In the Description, regarding the guide wire 100 and each constituent member thereof, an end on the distal end side is referred to as a "distal end", the distal end and a portion in the vicinity thereof are referred to as a "distal end portion", an end on the proximal end side is referred to as a "proximal end", and the proximal end and a portion in the vicinity thereof are referred to as a "proximal end portion". FIG. 1 shows a state where the guide wire 100 is in the form of a straight line substantially parallel to the Z axis direction, as a whole, but the configuration of at least a part of the guide wire 100 is flexible enough to be bent.

The guide wire 100 is a flexible, long medical device that is inserted into a blood vessel mainly for the purpose of penetrating a relatively hard lesion (for example, CTO) in a blood vessel. The full length of the guide wire 100 ranges from about 1500 mm to 2000 mm, for example.

The guide wire 100 includes a core shaft 10, a coil body 20, a distal end side joint part 30, a proximal end side joint part 40, an intermediate joint part 50, and a coat layer 60.

The core shaft 10 is configured of a large diameter portion 13 having a substantially constant outer diameter, a thin diameter portion 11 being located on the distal end side with respect to the large diameter portion 13 and having a substantially constant outer diameter smaller than that of the large diameter portion 13, and a tapered portion 12 being located between the large diameter portion 13 and the thin diameter portion 11 and having an outer diameter that gradually decreases from the boundary position thereof with the large diameter portion 13 to the boundary position thereof with the thin diameter portion 11. The shape of the transverse section (cross section XY) at each position of the core shaft 10 can have any shape, e.g., circular or flat-shaped. The outer diameter of the large diameter portion 13 ranges from about 0.2 mm to 0.8 mm, for example, and the outer diameter of the thin diameter portion 11 ranges from about 0.05 mm to 0.3 mm, for example.

Examples of materials to be used for forming the core shaft 10 include stainless steel (e.g., SUS302, SUS304 and SUS316), superelastic alloys such as an Ni—Ti alloy, and a piano wire. The core shaft 10 may be entirely formed of the same material or materials that differ from one portion to another.

The coil body 20 is a hollow cylindrical coiled member formed by tightly winding one wire spirally. The coil body 20 is arranged on the outer periphery of the core shaft 10 so as to cover the core shaft 10. In this embodiment, the coil body 20 covers, e.g., completely covers, the thin diameter portion 11 and the tapered portion 12 of the core shaft 10 and is joined to large diameter portion 13 at by the proximal end side joint part 40, e.g., adjacent to the boundary position between the tapered portion 12 and the large diameter portion 13.

Examples of materials to be used for forming the coil body 20 include radiolucent materials such as stainless steel (e.g., SUS302, SUS304, and SUS316), superelastic alloys e.g., an Ni—Ti alloy, and a piano wire, and radiopaque materials such as platinum, gold, tungsten or alloys thereof. The coil body 20 may be formed entirely of the same material or materials that differ from one portion to another.

The distal end side joint part 30 is a member that joins distal end of the coil body 20 and the distal end of the core shaft 10. Specifically, the distal end of the coil body 20 and the distal end of the core shaft 10 are fixed in such a manner that they are embedded inside the distal end side joint part 30. In other words, the distal end side joint part 30 completely covers the distal end of the coil body 20 and the distal end of the core shaft 10. The proximal end side joint part 40 is a member that joins the proximal end of the coil body 20 and the core shaft 10. The intermediate joint part 50 is a member that joins a portion between the distal end and the proximal end of the coil body 20 and the core shaft 10.

Examples of materials to be used for forming the distal end side joint part 30, the proximal end side joint part 40 and the intermediate joint part 50 include metal solders (e.g., Au—Sn alloy, Sn—Ag alloy, Sn—Pb alloy and Pb—Ag alloy), wax materials (e.g., aluminum alloy solder, silver solder and gold solder), and adhesives (e.g., epoxy-based adhesive). Materials for forming the distal end side joint part 30, the proximal end side joint part 40 and the intermediate joint part 50 may be the same or differ from each other. The distal end side joint part 30, the proximal end side joint part 40 and the intermediate joint part 50 may each be formed entirely of the same material or formed of materials that differ from one portion to another.

The coat layer 60 is arranged on the surface of the distal end side joint part 30. Examples of the material for forming the coat layer 60 include hydrophobic coating materials such as silicone oil and fluororesin, or hydrophilic coating materials such as polyvinyl pyrrolidone, polyacrylic acid, polyacrylamide, polyvinyl alcohol, maleic anhydride copolymer, and hyaluronic acid. The coat layer 60 may be hydrophilic in order to improve the penetration of the guide wire 100 into a lesion.

Figure 2:
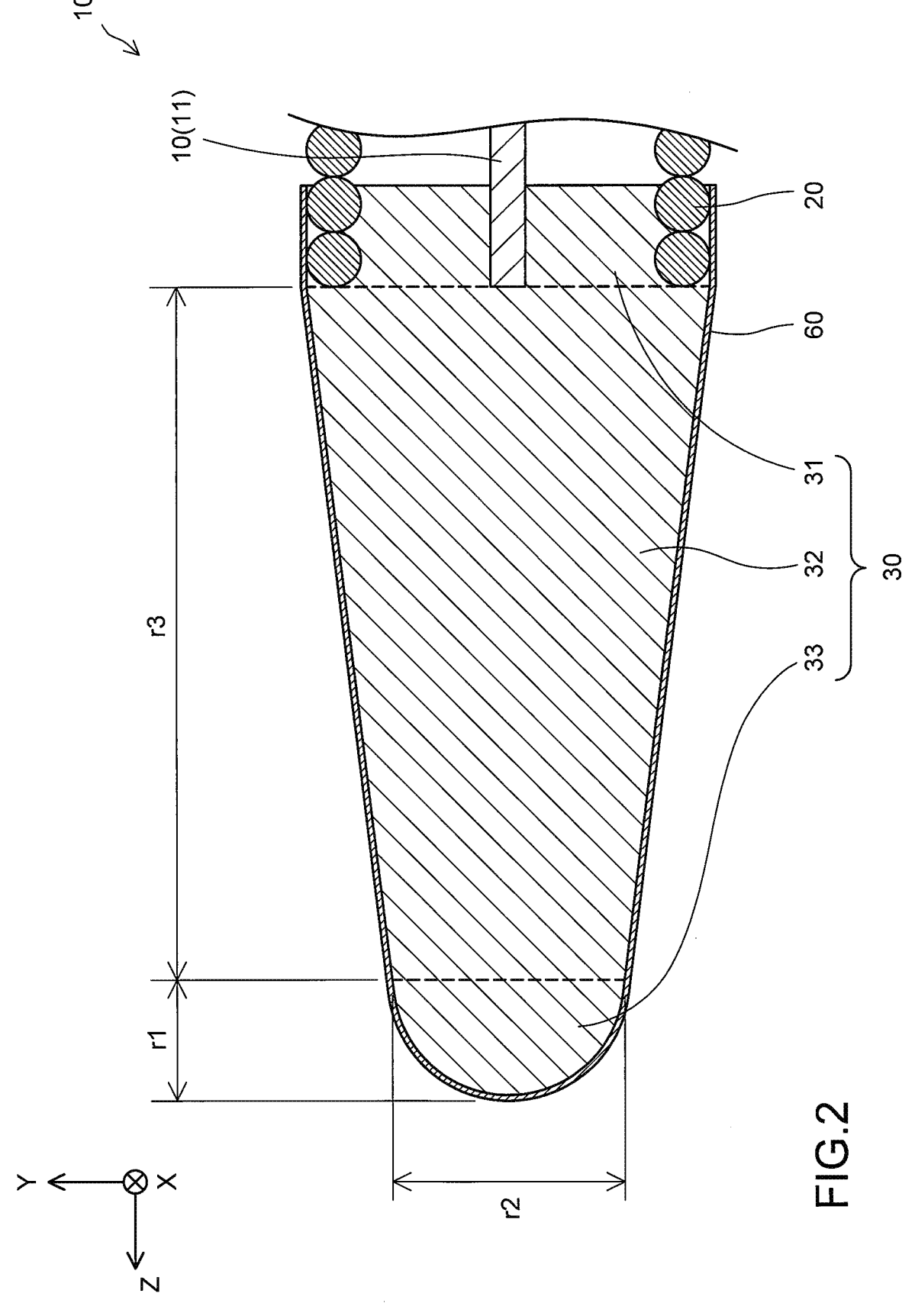
FIG. 2 is a diagram that shows the detailed configuration of the distal end side joint part of the guide wire shown in FIG. 1.

A-2. Detailed Configuration of Distal End Side Joint Part 30:

FIG. 2 is a diagram that shows a detailed configuration of the distal end side joint part 30, and is specifically an enlarged view of the longitudinal cross section (YZ cross section) thereof. The distal end side joint part 30 has a fixing part 31, an outer diameter decreasing portion 32, and a most distal end portion 33. The fixing part 31 is located on the most proximal end side in the distal end side joint part 30 and is a portion at which the distal end of the coil body 20 and the distal end of the core shaft 10 are fixed. The outer diameter decreasing portion 32 is located on the distal end side of the fixing part 31 in the distal end side joint part 30 and is a substantially truncated cone-shaped portion whose outer diameter decreases toward the distal end direction. The most distal end portion 33 is provided at the distal end of the outer diameter decreasing portion 32 in the distal end side joint part 30 and is a substantially spherical segment-shaped portion whose outer diameter decreases toward the distal end direction.

The outer diameter of the distal end of the outer diameter decreasing portion 32 and the outer diameter of the proximal end of the most distal end portion 33 are the same. Therefore, the shape of the distal end side joint part 30 smoothly changes from a shape in which the outer diameter linearly decreases toward the distal end direction in the outer diameter decreasing portion 32 to a shape in which the outer diameter decreases in a curve toward the distal end direction in the most distal end portion 33. The shape of the transverse section (XY cross section) of the outer diameter decreasing portion 32 and the most distal end portion 33 is substantially circular.

In the guide wire 100 of the embodiment, the height (the size in the direction from the distal end to the proximal end) r1 of the most distal end side portion 33, the outer diameter r2 of the bottom surface (the surface on the proximal end) of the most distal end side portion 33, and the height r3 of the outer diameter decreasing portion 32 of the distal end side joint part 30 satisfy the following equations (1) and (2). The outer diameter r2 of the bottom surface of the most distal end portion 33 is the same as the outer diameter of the top surface (the surface on the distal end) of the outer diameter decreasing portion 32. The outer diameter r2 of the bottom surface of the most distal end portion 33 may range from about 0.1 mm to 0.5 mm, for example.

$$0.33 < r1/r2 < 0.63 \qquad (1)$$

$$2.5 < r3/r2 < 3.8 \qquad (2)$$

Hereinafter, "r1/r2" in the above equation (1) is referred to as "most distal end portion ratio R1" and "r3/r2" in the above equation (2) is referred to as "outer diameter decreasing portion ratio R2". A large value of the most distal end portion ratio R1: r1/r2 indicates that the shape of the most distal end portion 33 is sharp (small surface area) and a large value of the outer diameter decreasing portion ratio R2: r3/r2 indicates that the shape of the outer diameter decreasing portion 32 is sharp. Therefore, the guide wire 100 satisfying the above equations (1) and (2) can be said as having a configuration in which the shape of the most distal end portion 33 is not too dull and not too sharp, and the shape of the outer diameter decreasing portion 32 is not too dull and not too sharp. Therefore, the guide wire 100 has such a configuration, so as to have an appropriate range of penetration performance such that it can reliably penetrate even a relatively hard lesion while avoiding damaging blood vessels.

A metal solder containing gold as a main component, such as an Au—Sn alloy, may be used as a material for forming the distal end side joint part 30. Such a metal solder containing gold as a main component is known to have high rigidity. When the distal end side joint part 30 is formed of such a metal solder containing gold as a main component, the distal end side joint part 30 can be provided with appropriate rigidity. The melting point of a metal solder containing gold as a main component, such as an Au—Sn alloy, is 400 degrees or lower. This can suppress a decrease in mechanical strength due to heat affection to the core shaft 10 and the coil body 20 when the distal end side joint part 30 is formed. A metal solder containing gold as a main component, such as an Au—Sn alloy, has excellent radiopacity. This can improve the visibility of the distal end side joint part 30 under a radioscopic image.

A-3. Method for Producing Guide Wire 100:

The guide wire 100 of the embodiment can be produced by the following method, for example. First, the core shaft 10 having a shape processed by mechanical polishing or the like and the coil body 20 manufactured by winding a coil wire are prepared. The core shaft 10 is inserted into the hollow part of the coil body 20, then a distal end side joint part 30, a proximal end side joint part 40, and an intermediate joint part 50 are formed for joining the coil body 20 and the core shaft 10. When the distal end side joint part 30 is formed, for example, a trowel or the like is used to roughly shape the joint part 30, so as to form precursors of the outer diameter decreasing portion 32 and the most distal end portion 33. Then, the surfaces of the precursors of the outer diameter decreasing portion 32 and the most distal end portion 33 are polished with a device such as a Leutor tool, thereby forming the outer diameter decreasing portion 32 and the most distal end portion 33 having shapes that satisfy the above equations (1) and (2). For example, the guide wire 100 having the above configuration can be produced by the method described above.

EXAMPLES

The penetration performance of the guide wire was evaluated. Subjected to evaluation were 30 types of guide wires having the same main configuration as that of the guide wire 100 of the embodiment described above, in which the value of the most distal end portion ratio R1: r1/r2 and the value of the outer diameter decreasing portion ratio R2: r3/r2 differ from each other in the distal end side joint part 30. In each guide wire, the outer diameter r2 of the bottom surface of the most distal end portion 33 ranged from 0.1 mm to 0.5 mm.

Figure 3:
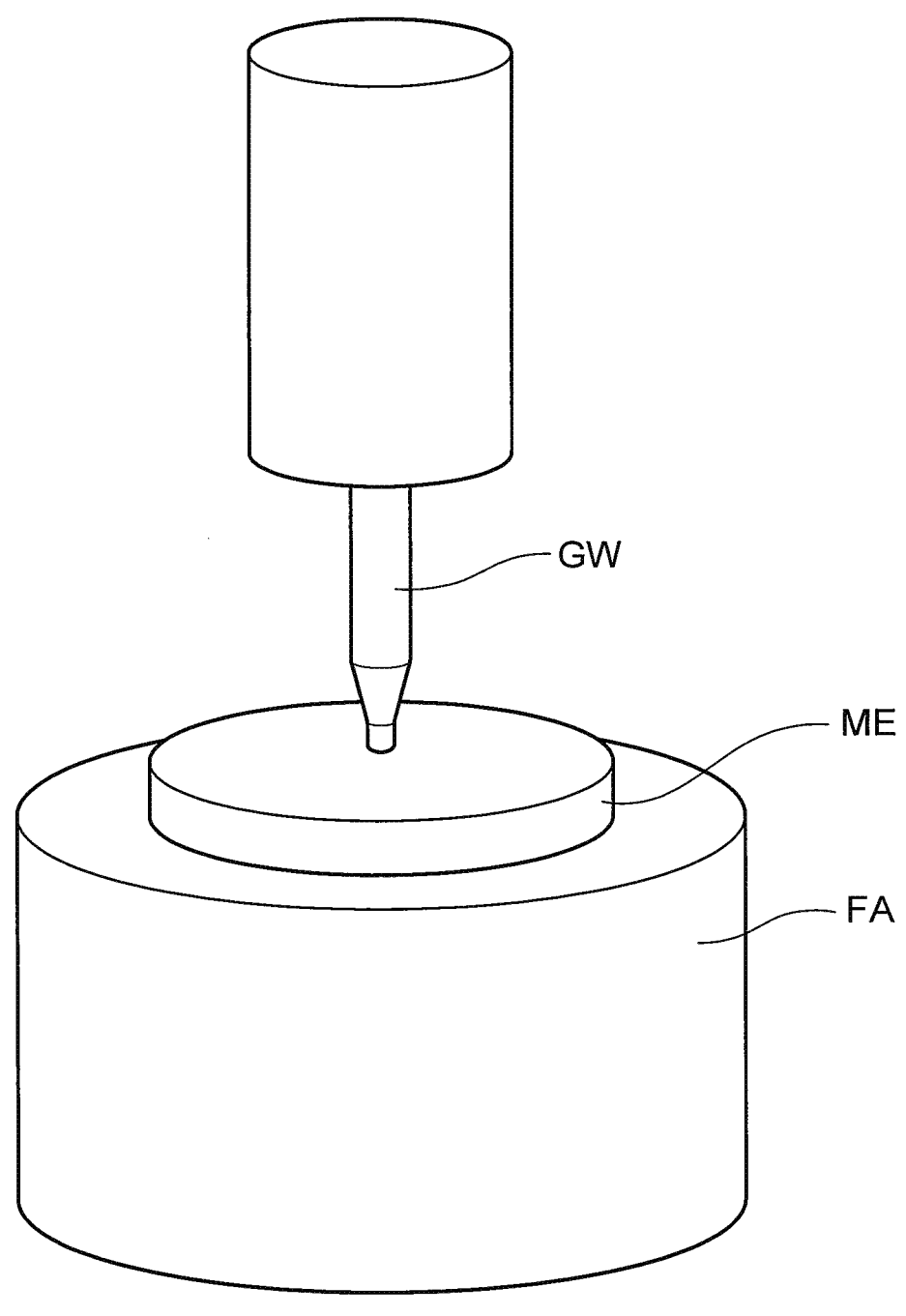
FIG. 3 is a diagram that shows a method for evaluating the penetration performance of guide wires.

FIG. 3 is a diagram that shows a method for evaluating the penetration performance of the guide wires. A membrane ME with a thickness of about 0.85 mm simulating a relatively hard lesion such as CTO was placed on a force analyzer FA for measuring the load. A guide wire GW having a length of about 1.5 mm was pierced with the distal end at the head into the membrane ME at a constant speed, and the load applied to the membrane ME was measured with a force analyzer FA, when the penetration depth d of the guide wire GW was 0.1 mm and when the same was 0.6 mm. The state where the penetration depth d is 0.1 mm is a state where almost the entire most distal end portion 33 of the distal end side joint part 30 is inserted into the membrane ME, and the state where the penetration depth d is 0.6 mm is a state where almost the entire most distal end portion 33 and the outer diameter decreasing portion 32 of the distal end side joint part 30 are inserted into the membrane ME. The load when the penetration depth d is 0.1 mm represents the ease with which the distal end of the guide wire GW can be pierced into a lesion. Specifically, the smaller the load when the penetration depth d is 0.1 mm, the easier it is for the distal end of the guide wire GW to be pierced into a lesion. The load when the penetration depth d is 0.6 mm represents the ease with which the distal end of the guide wire GW can advance further after piercing into a lesion. Specifically, the smaller the load when the penetration depth d is 0.6 mm, the easier it is for the guide wire GW to advance further after piercing into a lesion.

The appropriate load ranges RA (0.1) and RA (0.6) were set for the penetration depth d of 0.1 mm and for the penetration depth d of 0.6 mm respectively, based on the qualitative evaluation assuming clinical practice. Specifically, using a simulated lesion simulating CTO, a penetration test that involves penetrating a hard membrane on the surface of a simulated lesion and an operability test for the guide wire GW in the simulated lesion were conducted, and the appropriate load ranges RA (0.1) and RA (0.6) corresponding to not too low and not too high penetration performance were set based on the evaluation of a doctor.

Figure 4:
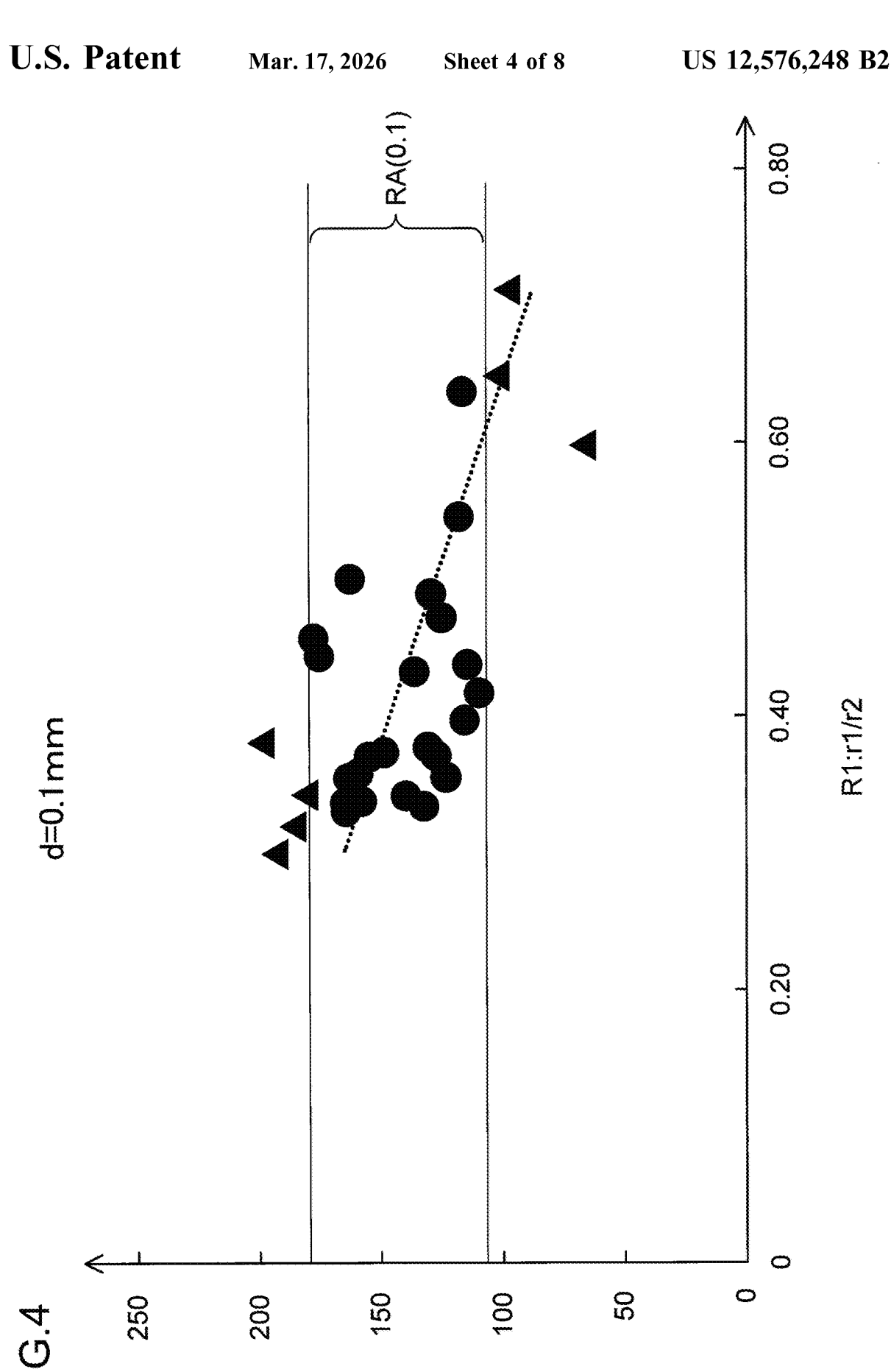
FIG. 4 is a graph showing the measurement results of the load applied to a membrane when a guide wire is inserted.
Figure 5:
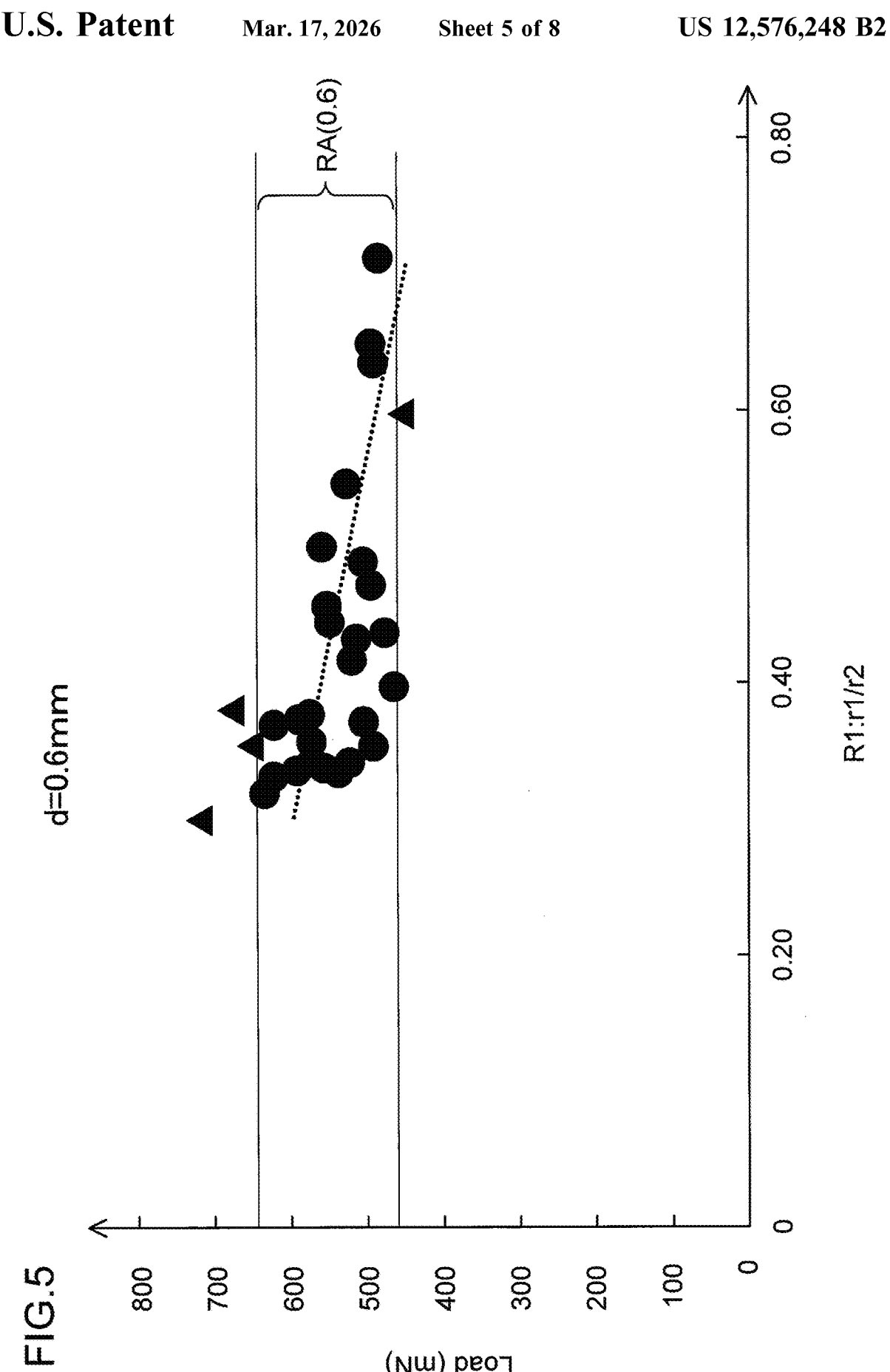
FIG. 5 is a graph showing the measurement results obtained under conditions differing from those under which the results in FIG. 4 were obtained.
Figure 6:
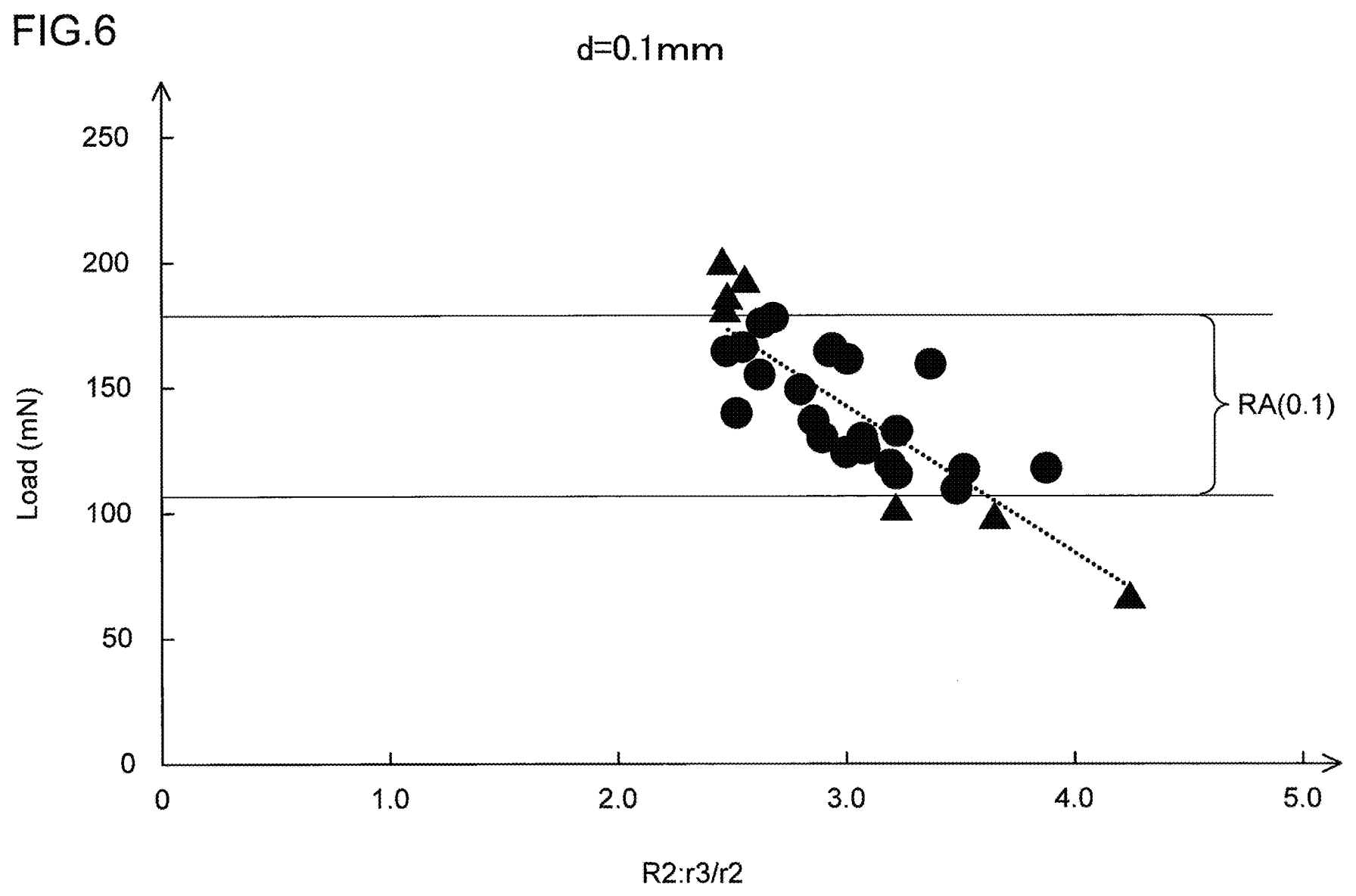
Figure 7:
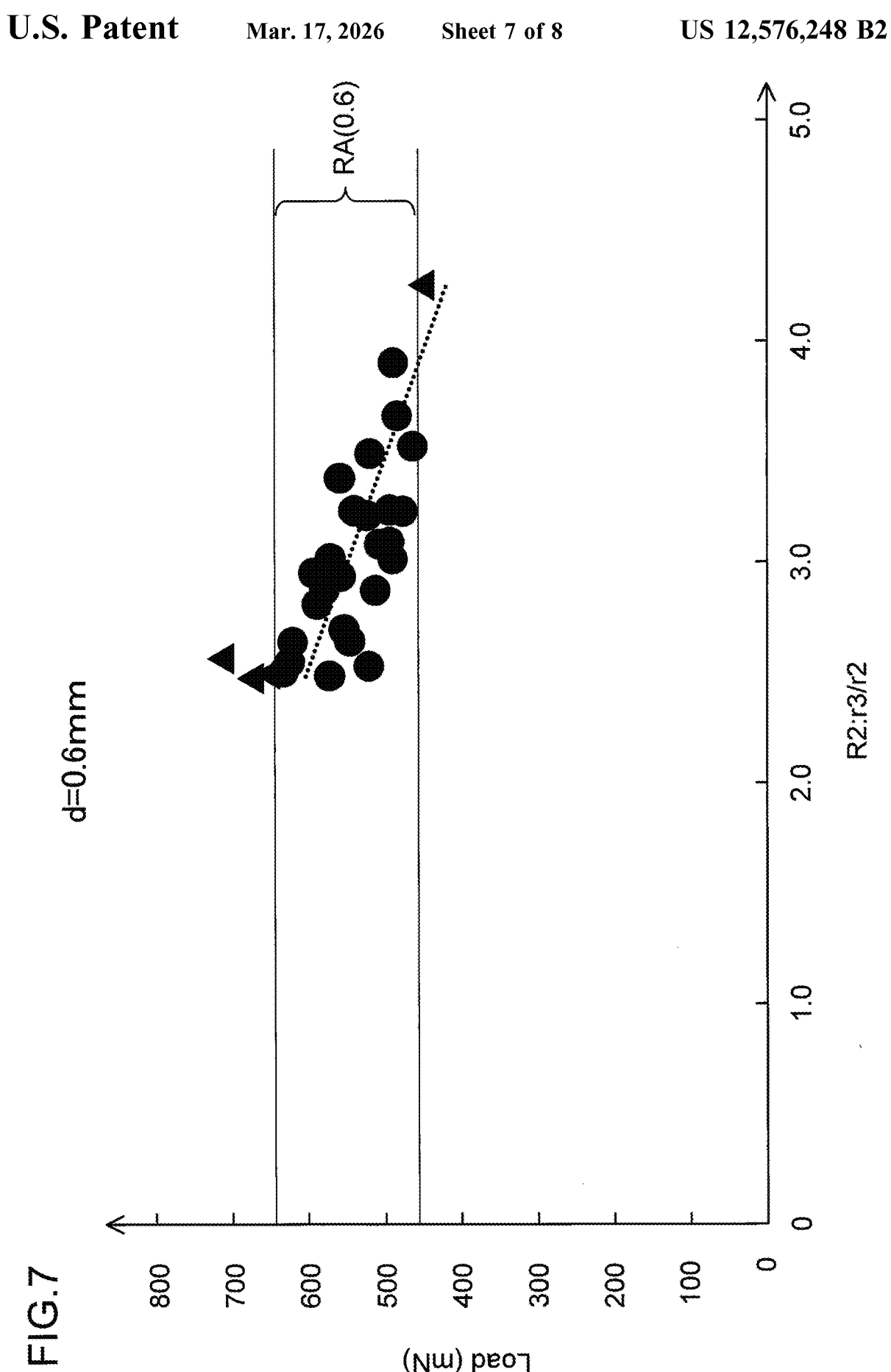
FIG. 7 is a graph showing the measurement results obtained under conditions same as those under which the results in FIG. 5 were obtained.

FIGS. 4 to 7 are graphs showing the results of measuring the load applied to the membrane ME when the guide wire GW was inserted. FIGS. 4 and 5 show the relationship between the most distal end portion ratio R1: r1/r2 and the load when the penetration depth d was 0.1 mm and the same when the penetration depth d was 0.6 mm. FIGS. 6 and 7 show the relationship between the outer diameter decreasing portion ratio R2: r3/r2 and the load when the penetration depth d was 0.1 mm and the same when the penetration depth d was 0.6 mm. With the values of most distal end portion ratio R1: r1/r2 or the outer diameter decreasing portion ratio R2: r3/r2 plotted on the horizontal axis, and with the values of the load plotted on the vertical axis, the measured value for each guide wire is plotted and the regression line derived from each measurement result is shown. The above appropriate load ranges RA (0.1) and RA (0.6) are shown, and values plotted within such range are indicated by black circles, and values plotted outside such range are indicated by black triangles.

As shown in FIGS. 4 and 5, it was confirmed that the load tends to decrease as the value of the most distal end portion ratio R1: r1/r2 increases at any time point when the penetration depth d was 0.1 mm or 0.6 mm. As described above, when the value of the most distal end portion ratio R1: r1/r2 is large, the shape of the most distal end portion 33 is sharp, so that the load applied by the guide wire GW to the membrane ME is considered to be small. Similarly, as shown in FIGS. 6 and 7, it was confirmed that the load tends to decrease as the value of the outer diameter decreasing portion ratio R2: r3/r2 increases at any time point when the penetration depth d was 0.1 mm or 0.6 mm. As described above, when the value of the outer diameter decreasing portion ratio R2: r3/r2 is large, the shape of the outer diameter decreasing portion ratio 32 is sharp, so that the load applied by the guide wire GW to the membrane ME is considered to be small.

Figure 8:
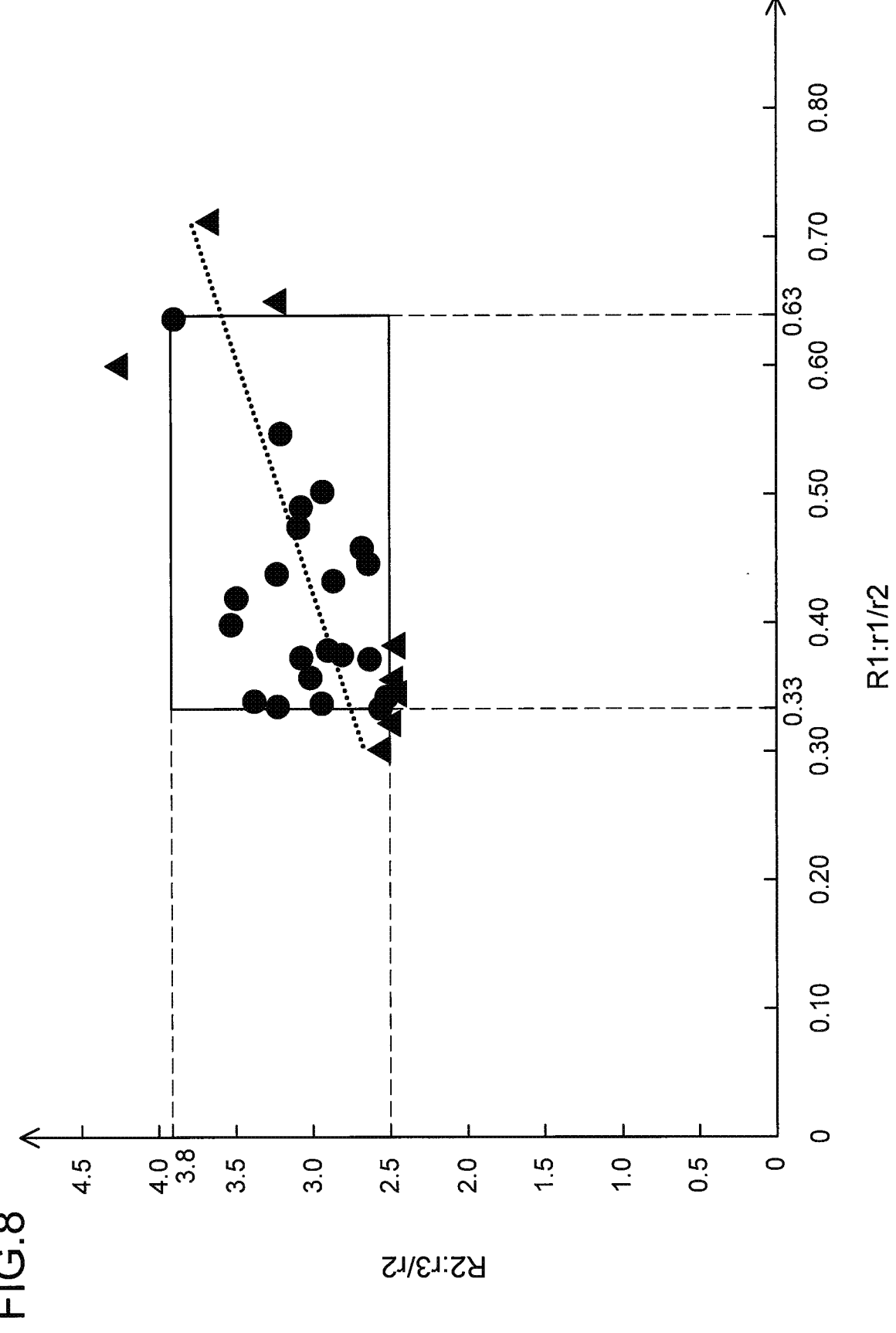
FIG. 8 is a graph showing the suitability of the load applied to a membrane in each combination of most distal end portion ratio R1 and outer diameter decreasing portion ratio R2.

FIG. 8 is a graph showing the suitability of the load applied to the membrane ME in each combination of the most distal end portion ratio R1 and the outer diameter decreasing portion ratio R2. With the values of the most distal end portion ratio R1: r1/r2 plotted on the horizontal axis, and with the values of the outer diameter decreasing portion ratio R2: r3/r2 plotted on the vertical axis, the measured value for each guide wire is plotted in this graph. For each combination of the most distal end portion ratio R1 and the outer diameter decreasing portion ratio R2, the values of the load plotted within the appropriate load ranges RA (0.1) and RA (0.6) in both cases of the penetration depth d of 0.1 mm and the penetration depth d of 0.6 mm are indicated by black circles, and the values of the load plotted outside the appropriate load ranges in one of or both cases of the penetration depth d of 0.1 mm and the penetration depth d of 0.6 mm are indicated by black triangles. As shown in FIG. 8, if the value of the most distal end portion ratio R1: r1/r2 was larger than 0.33 and smaller than 0.63, and the value of the outer diameter decreasing portion ratio R2: r3/r2 is larger than 2.5 and smaller than 3.8, the values of the load were within the appropriate ranges in both cases of the penetration depths d of 0.1 mm and 0.6 mm. Specifically, it can be said that when the above-mentioned equations (1) and (2) are satisfied, the values of the load are plotted within the appropriate ranges, and the penetration performance of the guide wire GW is within an appropriate range.

As described above, in the guide wire 100, if the height r1 of the most distal end portion 33, the outer diameter r2 of the bottom surface of the most distal end portion 33, and the height r3 of the outer diameter decreasing portion 32 of the distal end side joint part 30 satisfy the above equations (1) and (2), an appropriate range of penetration performance can be realized such that a relatively hard lesion can be reliably penetrated while avoiding damaging blood vessels.

B. Modification Example

The technology disclosed herein is not limited to the above-described embodiment, and can be modified in various forms without departing from the gist thereof. For example, the following modification examples are also possible.

The configuration of the guide wire 100 in the above embodiment is only an example and can be modified in various forms. In the above embodiment, the core shaft 10 is configured of the thin diameter portion 11, the tapered portion 12, and the large diameter portion 13. However, the core shaft 10 may not have at least one of these three parts, or may have other parts in addition to the parts.

In the guide wire 100 of the above embodiment, the proximal end side joint part 40 and the intermediate joint part 50 are provided, but at least one of these may be omitted.

In the guide wire 100 of the above embodiment, the coat layer 60 covers the surface of the distal end side joint part

30, but the coat layer 60 may cover the surface of the coil body 20 and the core shaft 10. The coat layer 60 may be omitted.

In the above embodiment, the coil body 20 covers the thin diameter portion 11 and the tapered portion 12 of the core shaft 10, but the portions of the core shaft 10 covered by the coil body 20 can be arbitrarily changed. For example, the coil body 20 may cover only the thin diameter portion 11 of the core shaft 10, or the coil body 20 may cover a part or all of the large diameter portion 13 in addition to the thin diameter portion 11 and the tapered portion 12 of the core shaft 10.

In the above embodiment, the coil body 20 is formed in a hollow cylindrical shape by tightly winding one wire spirally. However, the coil body 20 may be formed in a hollow cylindrical shape by roughly winding one wire, or may be formed in a hollow cylindrical shape by spirally winding a plurality of wires. The coil body 20 may be formed in a hollow cylindrical shape by spirally winding a single twisted wire formed by twisting a plurality of wires, or may be formed in a hollow cylindrical shape by spirally winding a plurality of twisted wires formed by twisting a plurality of wires.

The materials for each member in the above embodiment are only examples, and may be modified variously. The method for producing the guide wire in the above embodiment is only an example and can be modified variously. For example, in the above embodiment, the outer diameter decreasing portion 32 and the most distal end portion 33 of the distal end side joint part 30 are integrally formed. Alternatively, after the outer diameter decreasing portion 32 is formed, a precursor of the most distal end portion 33 may be formed at the distal end of the outer diameter decreasing portion 32 with a metal solder etc., and then the precursor may be polished to form the most distal end portion 33. In the above embodiment, the outer diameter decreasing portion 32 and the most distal end portion 33 having predetermined shapes are formed by polishing. Alternatively, the outer diameter decreasing portion 32 and the most distal end portion 33 may be formed by another known method (for example, casting).

The above embodiment is described using the guide wire for guiding a catheter to a target intravascular position as an example. The technology disclosed herein is also similarly applicable to a guide wire for guiding a medical device to a target position in a body cavity (e.g., blood vessel, gastrointestinal tract, and ureter).

REFERENCE SIGNS LIST

10 core shaft
11 thin diameter portion
12 tapered portion
13 large diameter portion
20 coil body
30 distal end side joint part
31 fixing part
32 outer diameter decreasing portion
33 most distal end portion
40 proximal end side joint part
50 intermediate joint part
60 coat layer
100 guide wire
FA force analyzer
GW guide wire
ME membrane

The invention claimed is:

1. A guide wire comprising:

a core shaft;

a coil body that covers the core shaft; and a distal end side joint that joins a distal end of the coil body and a distal end of the core shaft, wherein the distal end side joint includes:

a substantially truncated cone-shaped outer diameter decreasing portion whose outer diameter decreases toward a distal end thereof; and a substantially spherical segment-shaped most distal end portion at a distal end of the outer diameter decreasing portion having an outer diameter that decreases towards the distal end thereof, wherein a height r1 of the most distal end portion, an outer diameter r2 of a bottom surface of the most distal end portion, and a height r3 of the outer diameter decreasing portion satisfy equations (1) and (2):

$$0.33 < r1/r2 < 0.63 \qquad (1)$$

$$2.5 < r3/r2 < 3.8 \qquad (2).$$

2. The guide wire according to claim 1, further comprising a coat layer covering the distal end side joint.

3. The guide wire according to claim 2, wherein the coat layer and the distal end side joint together completely surround the distal end of the coil body and the distal end of the core shaft.

4. The guide wire according to claim 1, further comprising a proximal end side joint that joins a proximal end of the coil body and the core shaft.

5. The guide wire according to claim 1, further comprising an intermediate joint that joins the core shaft and a portion of the coil body between the distal end and a proximal end of the coil body.

6. The guide wire according to claim 1, wherein the core shaft includes:

a first portion having a substantially constant first outer diameter, a second portion located on the distal end side with respect to the first portion and having a substantially constant second outer diameter smaller than the first outer diameter, and a third portion between the first portion and the second portion 11 and having an outer diameter that gradually decreases from the first outer diameter to the second outer diameter.

7. The guide wire according to claim 6, further comprising a proximal end side joint that joins a proximal end of the coil body and the first portion.

8. The guide wire according to claim 7, wherein the proximal end side joint is located on the first portion adjacent to the third portion.

9. The guide wire according to claim 6, further comprising an intermediate joint that joins the second portion and a portion of the coil body between the distal end and a proximal end of the coil body.

10. The guide wire according to claim 1, wherein the distal end of the coil body and the distal end of the core shaft are embedded in the distal end side joint.

* * * * *